United States Patent
Imamura et al.

(10) Patent No.: US 9,689,384 B2
(45) Date of Patent: Jun. 27, 2017

(54) LIQUID FEED PUMP AND LIQUID CHROMATOGRAPH

(71) Applicant: SHIMADZU CORPORATION, Kyoto (JP)

(72) Inventors: Shinya Imamura, Kyoto (JP); Yoshiaki Maeda, Kyoto (JP)

(73) Assignee: SHIMADZU CORPORATION, Kyoto-shi (JP)

( * ) Notice: Subject to any disclaimer, the term of this patent is extended or adjusted under 35 U.S.C. 154(b) by 452 days.

(21) Appl. No.: 14/349,945

(22) PCT Filed: Dec. 12, 2012

(86) PCT No.: PCT/JP2012/082234
§ 371 (c)(1),
(2) Date: Apr. 4, 2014

(87) PCT Pub. No.: WO2013/089147
PCT Pub. Date: Jun. 20, 2013

(65) Prior Publication Data
US 2014/0260565 A1    Sep. 18, 2014

(30) Foreign Application Priority Data

Dec. 12, 2011 (WO) ................. PCT/JP2011/078654

(51) Int. Cl.
*F04B 53/02* (2006.01)
*F04B 13/00* (2006.01)
(Continued)

(52) U.S. Cl.
CPC ............. *F04B 53/02* (2013.01); *F04B 13/00* (2013.01); *F04B 53/143* (2013.01); *F04B 53/16* (2013.01);
(Continued)

(58) Field of Classification Search
None
See application file for complete search history.

(56) References Cited

U.S. PATENT DOCUMENTS 3,570,673 A * 3/1971 Dutz ...................... B01J 20/281
                                                                210/198.2
4,173,437 A    11/1979 Leka et al.
(Continued)

FOREIGN PATENT DOCUMENTS

CN    2057226 U    5/1990
CN    1490522 A    4/2004
(Continued)

OTHER PUBLICATIONS

HPLC Basics, Fundamentals of Liquid Chromatography (HPLC)—Courtesy of Agilent Technologies, Inc.. created Mar. 23, 2009.*
(Continued)

*Primary Examiner* — Paul West
*Assistant Examiner* — Mark A Shabman
(74) *Attorney, Agent, or Firm* — Westerman, Hattori, Daniels & Adrian, LLP

(57) ABSTRACT

A recess into which a protrusion of a plunger seal is to be fitted is provided at a part of a pump head where a plunger is to be inserted into a pump chamber. The plunger seal seals the pump chamber by an outer circumferential surface of the protrusion coming into close contact with an inner circumferential surface of the recess and a surface of a flange on the side of the protrusion coming into close contact with a circumferential edge surface of the recess of the pump head due to the protrusion being fitted into the recess and being pressed by a backup ring toward the pump chamber. The inner circumferential surface of the recess of the pump head and the circumferential edge surface of the recess are covered by a film of an acid-resistant material.

16 Claims, 6 Drawing Sheets

(51) Int. Cl.
*F04B 53/14* (2006.01)
*F04B 53/16* (2006.01)
*G01N 30/28* (2006.01)
*G01N 30/32* (2006.01)

(52) U.S. Cl.
CPC ........... *F04B 53/164* (2013.01); *G01N 30/28* (2013.01); *G01N 30/32* (2013.01); *G01N 2030/326* (2013.01)

(56) References Cited

U.S. PATENT DOCUMENTS

| 4,699,717 | A | * | 10/1987 | Riesner | ................. | B01D 15/08 |
| | | | | | | 210/198.2 |
| 2005/0095145 | A1 | | 5/2005 | Hiraku et al. | | |
| 2011/0164996 | A1 | | 7/2011 | Imamura | | |

FOREIGN PATENT DOCUMENTS

| CN | 2869375 Y | 2/2007 |
| CN | 102116288 A | 7/2011 |
| EP | 0095448 A1 | 11/1983 |
| GB | 1000529 A | 8/1965 |
| JP | 54-26507 | 2/1979 |
| JP | 60-175781 A | 9/1985 |
| JP | 5-13735 U | 2/1993 |
| JP | 8-4957 A | 1/1996 |
| JP | 2000-28464 A | 1/2000 |
| JP | 2001-254686 A | 9/2001 |
| JP | 2004-294204 A | 10/2004 |
| JP | 2008-180088 A | 7/2008 |
| JP | 2008-180088 A | 8/2008 |
| JP | 2011-13045 A | 1/2011 |

OTHER PUBLICATIONS

International Search Report dated Mar. 12, 2013 issued in corresponding application No. PCT/JP2012/082234.
Office Action dated Aug. 3, 2015, issued in counterpart Chinese Patent Application No. 2012800592304, with English translation (10 pages).
Office Action dated May 24, 2016, issued in counterpart Chinese Patent Application No. 201280059230.4, with English ranslation. (7 pages).
Office Action and Search Report dated Oct. 27, 2016, issued in counterpart Chinese Application No. 201280059230.4, with English translation. (13 pages).

* cited by examiner

LIQUID FEED PUMP AND LIQUID CHROMATOGRAPH

TECHNICAL FIELD

The present invention relates to a liquid feed pump for feeding liquid by repeating suction of liquid from a suction port and discharge of liquid from a discharge port by sliding a plunger inside a pump head, and a liquid chromatograph that uses the liquid feed pump.

BACKGROUND ART

A schematic cross-sectional diagram of a pump chamber and its periphery of a general liquid feed pump is shown in FIG. 4.

A pump body 18 and a pump head 8 are provided. Although not shown, a crosshead that reciprocates in one direction (the left/right direction in the drawing) by a cam mechanism is accommodated inside the pump body 18, and a plunger 3 is held at a tip end of the crosshead. The plunger 3 reciprocates in the axial direction according to the movement of the crosshead.

The pump head 8 is provided with a pump chamber 8a for storing suctioned liquid, and a suction port 8b and a discharge port 8c that are paths that communicate with the pump chamber 8a from the outside. A tip end of the plunger 3 penetrates a tip end of the pump body 18, and is inserted into the pump chamber 8a inside the pump head 8. Suction of liquid from the suction port 8b and discharge of liquid from the discharge port 8c are performed by a tip end portion of the plunger 3 sliding inside the pump chamber 8a.

With such a liquid feed pump, a plunger seal 13 for preventing leakage of liquid from a gap between an inner wall of the pump chamber 8a and an outer circumference of the plunger 3 is attached to a portion of the pump chamber 8a into which the plunger 3 is to be inserted (for example, see Patent Document 1). The plunger seal 13 is a ring-shaped resin material having a penetration hole through which the plunger 3 is to penetrate.

The plunger seal 13 is sandwiched between the pump head 8 and the pump body 18 for holding the pump head 8. Also, a backup ring for improving the sealing performance of the plunger seal 13 is sometimes inserted at the back side of the plunger seal 13. In this case, the plunger seal 13 is sandwiched between the backup ring and the pump head. The backup ring is biased toward the plunger seal 13 by the pump body, and the plunger seal 13 is biased toward the pump head 8 by the backup ring.

PRIOR ART DOCUMENT

Patent Document

Patent Document 1: Japanese Patent Laid-open Publication No. 2001-254686

SUMMARY OF THE INVENTION

Problems to be Solved by the Invention

Generally, the plunger seal 13 is configured of a cylindrical protrusion protruding toward the side of the pump head along the axial direction of the penetration hole provided at the center, and a flange provided at the base end of the protrusion. A seal attachment portion of the pump head 8 for attaching the plunger seal 13 is provided with a recess for fitting the protrusion of the plunger seal 13. The plunger seal 13 attached to the seal attachment portion prevents leakage of liquid from the pump chamber 8a by the outer circumferential surface of the protrusion coming into close contact with the inner circumferential surface of the recess of the seal attachment portion, and the flange coming into close contact with the surface around the recess of the seal attachment portion.

When the plunger 3 is driven, since the inner circumferential surface of the plunger seal 13 which slides against the outer circumferential surface of the plunger 3 is softer than a material of the plunger 3, it tends to be worn. On the other hand, since the outer circumferential surface and the flange of the plunger seal 13 do not slide against the wall surface of the pump head 8, the outer circumferential surface of the plunger seal 13 is not worn. Thus, it was assumed that liquid does not leak from the outer side of the plunger seal 13.

However, when the wear of the inner circumferential surface of the plunger seal 13 progresses, the plunger seal 13 becomes more likely to move according to the reciprocation of the plunger 3, and a slight gap is created between the plunger seal 13 and the wall surface of the pump head 8. As a mobile phase, mixed liquid of highly volatile acid (for example, trifluoroacetic acid, acetic acid, formic acid or the like) and organic solvent is sometimes used. It was found that when this mixed liquid permeates into the gap between the plunger seal 13 and the pump head 8, only the solvent component vaporizes and the metal wall surface of the pump head 8 may be corroded or etched by the acid left in the gap. When the metal wall surface of the pump head 8 is corroded or etched, liquid will leak from between the plunger seal 13 and the wall surface of the pump head 8.

Accordingly, the present invention has its object to prevent corrosion or etching of the wall surface of the pump head, and to prevent decrease in the sealing performance of the plunger seal.

Solutions to the Problems

A liquid feed pump of the present invention includes a pump head including a liquid inlet for drawing liquid in, a pump chamber for storing the liquid drawn in from the liquid inlet, and a liquid outlet for discharging the liquid inside the pump chamber, a plunger for sliding inside the pump head with a tip end side inserted in the pump head, a plunger seal, formed into a ring shape, for sealing a gap between the pump head and the plunger while holding the plunger by a hole at a center, and a seal attachment portion, provided at a portion of the pump head where the plunger is inserted into the pump chamber, including a wall surface for receiving the plunger seal, the wall surface being covered by a film of an acid-resistant material.

The "ring shape" does not refer to the precise shape, but refers to the shape of a rotating body having a hole at the center through which the plunger is to pass, the rotating body having a predetermined thickness. The "ring shape" is used in the sense of including one that has a flange, as shown in an embodiment, extending out the body of the ring.

An acid-resistant material is used so that usage in a case where liquid to be delivered includes acid is also possible.

A liquid chromatograph of the present invention includes an analytical path, a liquid feed pump for feeding a mobile phase to the analytical path, a sample injection section for injecting a sample into the analytical path, an analytical column provided on the analytical path, on a downstream side of the sample injection section, the analytical column being for separating the sample into each component, and a detector provided on the analytical path, on a downstream side of the analytical column, the detector being for detecting the component separated by the analytical column, where a liquid feed pump of the present invention is used as the liquid feed pump.

Effects of the Invention

With the liquid feed pump of the present invention, the wall surface, for receiving the plunger seal, of the seal attachment portion for attaching the plunger seal is covered by a film of an acid-resistant material, and thus, even if liquid including acid permeates into the gap between the plunger seal and the wall surface of the pump head, corrosion or etching of the wall surface of the pump head by the acid is prevented. Accordingly, liquid may be fed with high accuracy over a long period of time.

The liquid chromatograph of the present invention uses the liquid feed pump of the present invention that achieves the effect described above, and thus, high feeding accuracy may be maintained over a long period of time, and the reliability of the analysis result may be improved.

EMBODIMENTS OF THE INVENTION

According to a preferred embodiment of the present invention, as an acid-resistant material, a material selected from a group consisting of noble metals, diamond-like carbon (hereinafter DLC), and engineering plastics having resistance to acid may be used.

A noble metal suitable as the acid-resistant material is gold, platinum, rhodium, or iridium. Noble metals include eight types of metals, i.e. gold, silver, ruthenium, rhodium, palladium, osmium, iridium, and platinum, and among these metals, gold, platinum, rhodium, and iridium are particularly superior in acid resistance, and are suitable as the material for a film for preventing corrosion or etching of a wall surface of a pump head.

Also, as the engineering plastic having resistance to acid, polyamide (PA), ultrahigh molecular weight polyethylene (U-PE), polyethersulfone (PES), polyphenylene sulfide (PPS), polyacrylate (PAR), polyamideimide (PAI), polyether ether ketone (PEEK), polytetrafluoroethylene (PTFE), liquid crystal polymer (LCP), polyvinylidene fluoride (PVDF), and the like may be used.

Since the pump head is formed of metal such as stainless steel, the wall surface on the inner side of the pump chamber is a metal surface. On the other hand, a plunger is formed of ceramics or sapphire. Accordingly, the plunger whose outer circumferential surface slides against the wall surface on the inner side of the pump chamber is a consumable which needs to be replaced due to wear after being used for a predetermined period of time.

A film of an acid-resistant material, therefore, may also be formed on the wall surface inside the pump chamber as well as on a seal attachment portion. By covering the wall surface on the inner side of the pump chamber, which is a metal surface, by a film of an acid-resistant material, wear of the plunger which slides against the wall surface on the inner side of the pump chamber may be suppressed, and the life of the plunger may be made longer. Particularly, the frictional coefficient of diamond-like carbon is low, and thus, the frictional force at the time of the plunger coming into contact with the wall surface of the pump chamber is small, and the life of the plunger may be made longer, and the load on a motor driving the plunger may be made small.

In the following, an embodiment of a liquid feed pump will be described with reference to FIGS. 1A, 1B, and 1C.

Figure 1A:
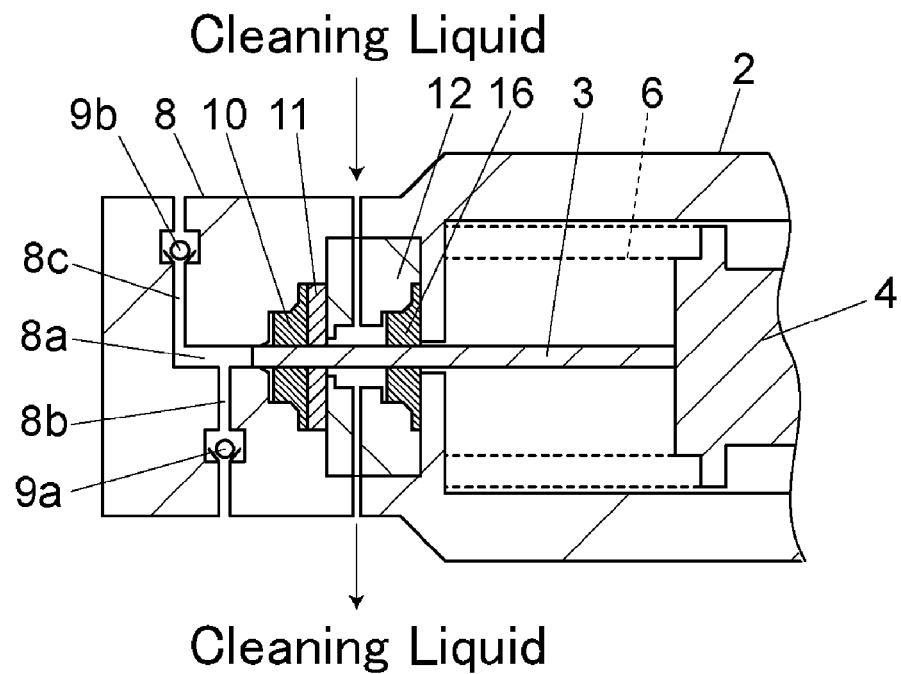
FIG. 1A is a cross-sectional diagram of a part, at a tip end side, of a pump body according to an embodiment of a liquid feed pump.
Figure 1B:
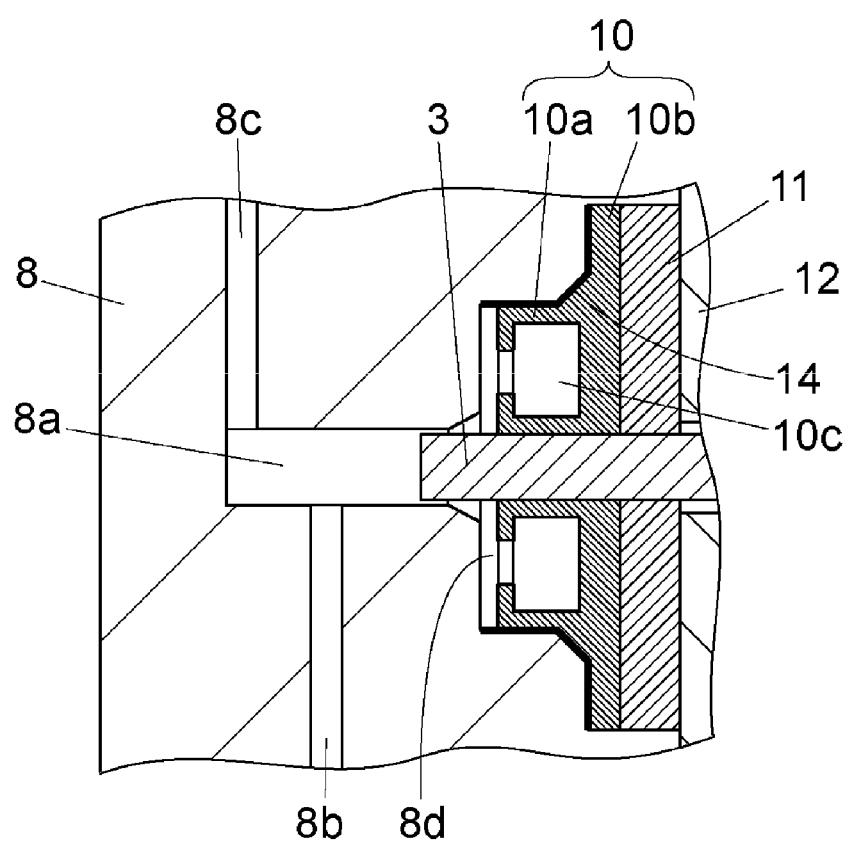
FIG. 1B is a cross-sectional diagram showing a pump chamber according to the embodiment and its periphery in an enlarged manner.
Figure 1C:
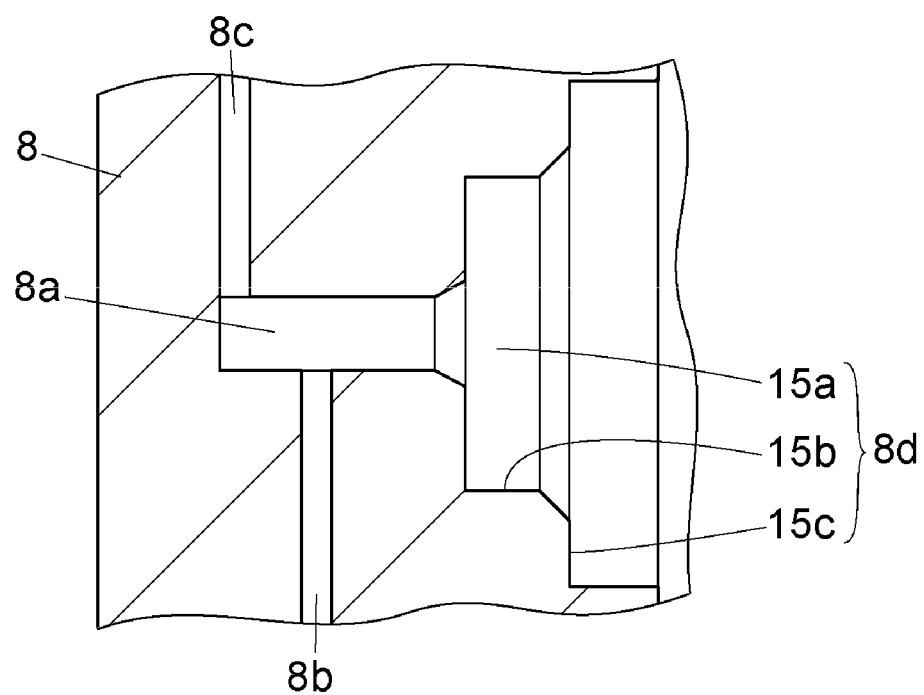
FIG. 1C is a cross-sectional diagram showing the pump chamber according to the embodiment and its periphery in an enlarged manner, where a film of an acid-resistant material is not formed and where a plunger seal and a backup ring are not attached.

First, as shown in FIG. 1A, a liquid feed pump of the embodiment is configured by having a pump head 8 attached to a tip end of a pump body 2 across a cleaning chamber 12. A pump chamber 8a is provided inside the pump head 8. A crosshead 4 is accommodated inside the pump body 2 in a movable manner.

The crosshead 4 is biased in a direction away from the pump head 8 (in the right direction in the drawing) by an elastic body 6 such as a spring. Although not shown, a cam mechanism is provided at a base-end portion side of the crosshead 4. The cam mechanism is a mechanism for rotating a cam by a drive mechanism such as a motor. Since the crosshead 4 is biased toward the cam mechanism by the elastic body 6, the base end portion of the crosshead 4 follows the circumferential surface of the rotating cam. Then, the crosshead 4 reciprocates, in the pump body 2, in directions toward and away from the pump head 8 (the left/right direction in the drawing) according to the rotation of the cam.

A base end portion of the plunger 3 is held at the tip end of the crosshead 4. A tip end portion of the plunger 3 penetrates the tip end of the pump body 2 and the cleaning chamber 12, and is inserted into the pump chamber 8a inside the pump head 8. The tip end portion of the plunger 3 slides along the wall surface of the pump chamber 8a according to the movement of the crosshead 4.

The pump head 8 is also provided with a liquid inlet path 8b for drawing liquid into the pump chamber 8a, and a liquid outlet path 8c for pushing liquid out of the pump chamber 8a. The liquid inlet path 8b is provided with a check valve 9a formed of a ball-shaped disc and a seat on which the disc is to be seated. Also, the liquid outlet path 8c is provided with a check valve 9b having the same structure as the check valve 9a. Additionally, in the drawing, the check valves 9a and 9b are provided as a part of the pump head 8, but they may alternatively be attached to the pump head 8 from the outside.

When the plunger 3 is driven in the direction away from the pump chamber 8a (in the right direction in the drawing), and the pressure inside the pump chamber 8a is reduced, the check valve 9b is closed and the check valve 9a is opened, and liquid is drawn into the pump chamber 8a from the liquid inlet path 8b. On the other hand, when the plunger 3 is driven in the direction of insertion into the pump chamber

8a (in the left direction in the drawing), and the pressure inside the pump chamber 8a is increased, the check valve 9a is closed and the check valve 9b is opened, and liquid is pushed out of the pump chamber 8a into the liquid outlet path 8c. Feeding of liquid is performed by the repetition of such a movement.

A plunger seal 10 is attached to the pump chamber 8a, at the insertion portion for the plunger 3. A backup ring 11 is inserted at the back side of the plunger seal 10 (on the side of the pump body 2). The plunger seal 10 is for preventing leakage of liquid from the gap between the inner wall of the pump chamber 8a and the circumferential surface of the plunger 3. The back side of the backup ring 11 is supported by the wall surface of the cleaning chamber 12. The plunger seal 10 is biased by the backup ring 11 toward the pump chamber 8a.

The cleaning chamber 12 includes, on the inside, a path for letting cleaning liquid pass, and a space for cleaning the outer circumferential surface of the penetrating plunger 3 by the cleaning liquid. At the insertion portion for the plunger 3 in the inner space of the cleaning chamber 12, a cleaning seal 16 for slidably holding the outer circumferential surface of the plunger 3 is provided to prevent leakage of the cleaning liquid. The back side of the cleaning seal 16 is supported by the wall surface of the pump body 2.

An attachment portion for the plunger seal 10 will be described with reference to FIGS. 1B and 1C. The plunger seal 10 is configured from an elastic material such as polyethylene resin, for example, and is a ring-shaped member having a hole for letting the plunger 3 pass through. At the center of the plunger seal 10, a cylindrical protrusion 10a that protrudes in the axial direction of the plunger 3, and a flange 10b that is provided at the base end of the protrusion 10a are provided. A space 10c having a rectangular cross section and opened along the circumference of the protrusion 10a is provided to the protrusion 10a, on the side of the pump chamber 8a. The space 10c is provided with the aim of storing liquid which has leaked from between the inner wall of the pump chamber 8a and the outer circumference of the plunger 3, and of improving the contact between the plunger seal 10 and the inner wall surface of the pump head 8 or the plunger 3 by using a rise in the pressure inside the pump chamber 8a.

As shown in FIG. 10, a seal attachment portion 8d including a recess 15a into which the protrusion 10a of the plunger seal 10 is to be fitted is provided at a part of the pump head 8 where the plunger 3 is to be inserted into the pump chamber 8a. The protrusion 10a of the plunger seal 10 attached to the seal attachment portion 8d is fitted into the recess 15a, and the outer circumferential surface of the protrusion 10a comes into close contact with an inner circumferential surface 15b of the recess 15a. Moreover, the surface of the flange 10b on the side of the protrusion 10a comes into close contact with a wall surface 15c around the seal attachment portion 8d by the back side of the flange 10b of the plunger seal 10 being pressed by the backup ring 11 toward the pump chamber 8a. The plunger seal 10 thereby seals the pump chamber 8a.

The inner circumferential surface 15b of the recess 15a of the seal attachment portion 8d that is to come into close contact with the plunger seal 10, and the surface 15c around the recess 15a are covered by a film 14 (shown by a thick line in FIG. 1B) of an acid-resistant material. In this embodiment, the diameter of the plunger 3 is 2 mm, and the diameter of the recess 8d is 4 mm. In this case, the thickness of the film 14 of an acid-resistant material is, for example, about 3 μm. As the material of the film 14 of an acid-resistant material, a noble metal such as gold, platinum, rhodium or iridium, or DLC, for example may be used.

The film 14 of an acid-resistant material which is of the noble metal or the DLC as mentioned above may be formed by, for example, a PVD (physical vapor deposition) process, a CVD (chemical vapor deposition) process, or an ionized deposition method.

It is also possible to use an engineering plastic superior in chemical resistance such as PEEK or PTFE as the material for the film 14 of an acid-resistant material. The film 14 of an acid-resistant material formed of an engineering plastic such as PEEK or PTFE may be formed by powder coating.

Figure 2:
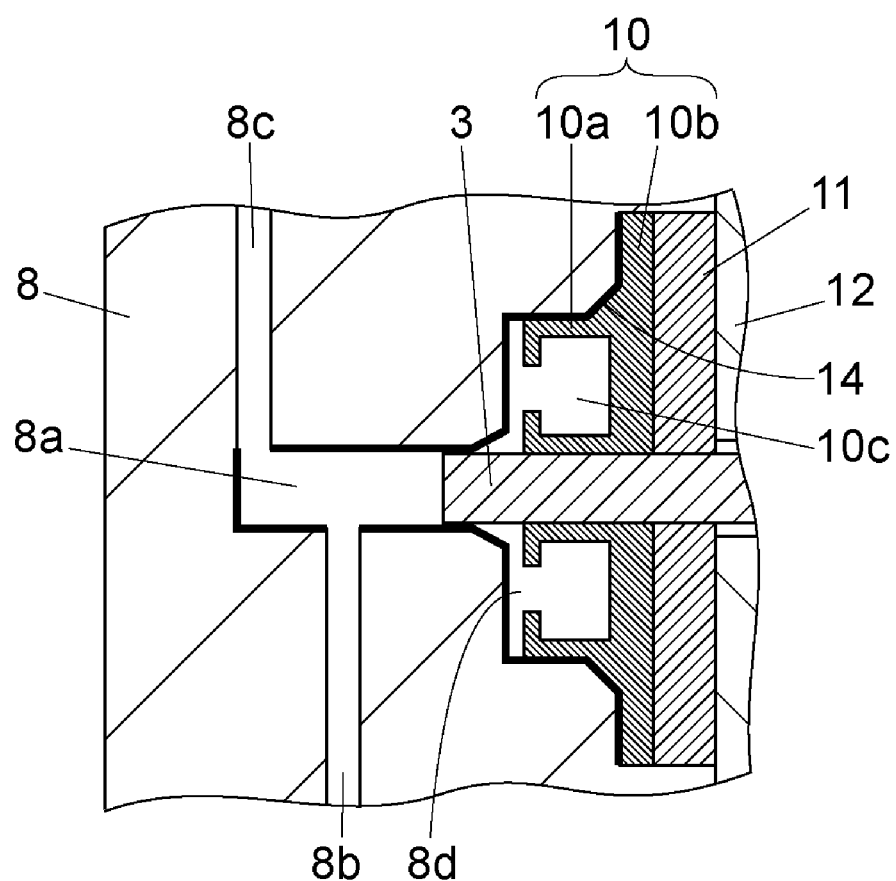
FIG. 2 is a cross-sectional diagram showing a pump chamber of another embodiment of the liquid feed pump and its periphery.

As shown by a thick line in FIG. 2, the film 14 of an acid-resistant material may also be formed on the inner surface of the pump chamber 8a. In this embodiment, the film 14 of an acid-resistant material is formed on the inner circumferential surface and the bottom surface of the pump chamber 8a. The DLC is especially superior in wear resistance with a low frictional coefficient of 0.1, and thus, by forming a DLC film on the inner surface of the pump chamber 8a, the frictional force at the time of the plunger 3 coming into contact with the wall surface of the pump chamber 8a is made small, and the load on a motor for driving the plunger 3 is made small. Additionally, also in this case, the film 14 of an acid-resistant material may be formed of a noble metal such as gold, platinum, rhodium or iridium, or an engineering plastic such as PEEK or PTFE.

Figure 3:
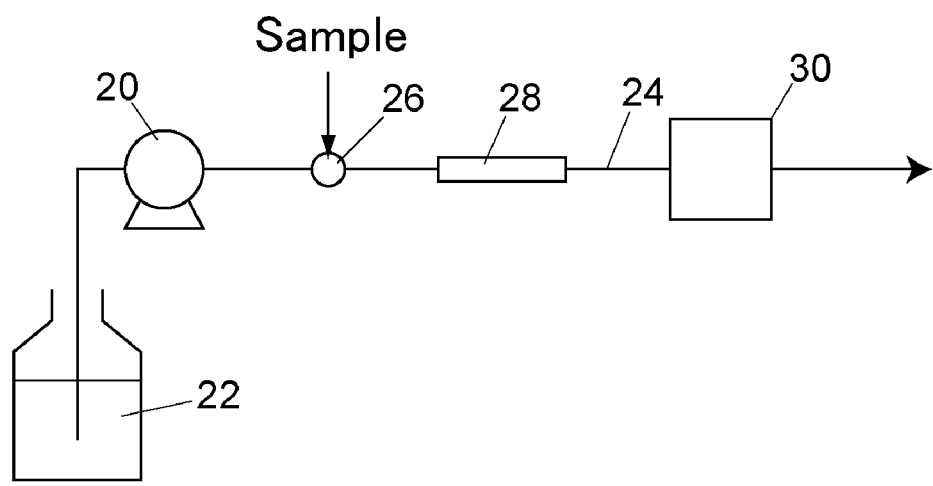
FIG. 3 is a path diagram schematically showing an embodiment of a liquid chromatograph.
Figure 4:
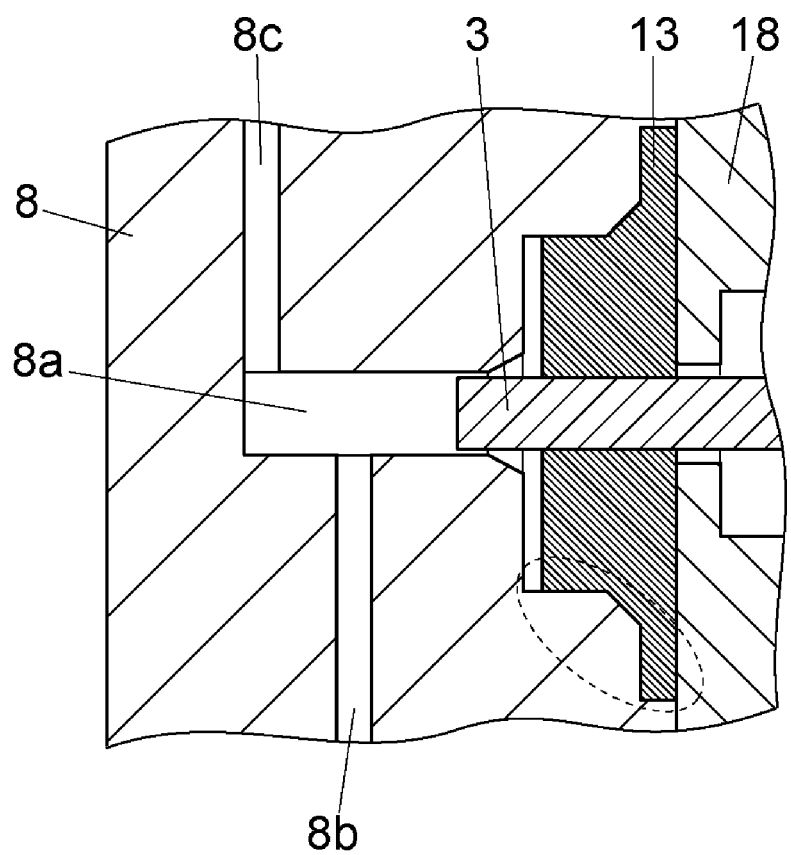
FIG. 4 is a cross-sectional diagram showing a pump chamber of an example of a conventional liquid feed pump and its periphery.

An embodiment of a liquid chromatograph that uses the liquid feed pump of the embodiment described above will be described with reference to FIG. 3. A liquid feed pump 20 is provided on an analytical path 24. The liquid feed pump 20 feeds a mobile phase 22 in the analytical path 24. A sample injection section 26 is provided on the analytical path 24, on the downstream side of the liquid feed pump 20. An analytical column 28 is provided on the analytical path 24, on the downstream side of the sample injection section 26. A detector 30 is provided on the analytical path 24, on the downstream side of the analytical column 28.

The sample injection section 26 is realized by, for example, one port (an injection port) among a plurality of ports provided to a switching valve forming an auto-sampler. In this case, injection of a sample into the sample injection section 26 is performed by a needle of the auto-sampler. The injected sample is temporarily retained in a sample loop. Then, when the analytical path 24 is formed by the switching valve being switched, and the mobile phase 22 is fed by the liquid feed pump 20, the sample retained in the sample loop is lead to the analytical column 28. In the analytical column 28, the sample is separated into each component, and each component is detected by the detector 30.

With the liquid chromatograph, the flow rate of the mobile phase flowing through the analytical path affects a detection signal that is obtained by the detector 30, and thus, the feeding flow rate of the mobile phase has to be accurately maintained. In this example, the liquid feed pump of the embodiment in FIG. 1A to 1C or 2 is used as the liquid feed pump 20, and thus, even if liquid including acid is used as the mobile phase, the metal wall surface of the plunger seal attachment portion of the pump head of the liquid feed pump is not corroded or etched by acid, and leakage of liquid from the outer circumference of the plunger seal is prevented, and the feeding accuracy of the liquid feed pump is maintained over a long period of time. Accordingly, the reliability of the analysis result of the liquid chromatograph is improved.

DESCRIPTION OF REFERENCE SIGNS

2: Pump body
3: Plunger

4: Crosshead
6: Elastic body
8: Pump head
8a: Pump chamber
8b: Liquid inlet path
8c: Liquid outlet path
8d: Seal attachment portion
9a, 9b: Check valve
10: Plunger seal
10a: Protrusion
10b: Flange
11: Backup ring
12: Cleaning chamber
14: Film of acid-resistant material
15a: Recess of seal attachment portion
15b: Inner circumferential surface of recess
15c: Surface around recess
16: Cleaning seal

The invention claimed is:

1. A liquid feed pump comprising:
a pump head including a liquid inlet for drawing liquid in, a pump chamber for storing the liquid drawn in from the liquid inlet, and a liquid outlet for discharging the liquid inside the pump chamber;
a plunger for sliding inside the pump head with a tip end side inserted in the pump head;
a plunger seal, formed into a ring shape, for sealing a gap between the pump head and the plunger while holding the plunger by a hole at a center; and
a seal attachment portion, provided at a portion of the pump head where the plunger is inserted into the pump chamber, including a wall surface which is in close contact with the plunger seal, the wall surface being covered by a film of an acid-resistant material.

2. The liquid feed pump according to claim 1, wherein the acid-resistant material is a material selected from a group consisting of a noble metal, diamond-like carbon, and an engineering plastic having resistance to acid.

3. The liquid feed pump according to claim 2, wherein the noble metal is a material selected from a group consisting of gold, platinum, rhodium, and iridium.

4. The liquid feed pump according to claim 3, wherein the film of the acid-resistant material is formed also on a wall surface inside the pump chamber.

5. A liquid chromatograph comprising:
an analytical path;
the liquid feed pump according to claim 4, the liquid feed pump being for feeding a mobile phase to the analytical path;
a sample injection section for injecting a sample into the analytical path;
an analytical column provided on the analytical path, on a downstream side of the sample injection section, the analytical column being for separating the sample into each component; and
a detector provided on the analytical path, on a downstream side of the analytical column, the detector being for detecting the component separated by the analytical column.

6. A liquid chromatograph comprising:
an analytical path;
the liquid feed pump according to claim 3, the liquid feed pump being for feeding a mobile phase to the analytical path;
a sample injection section for injecting a sample into the analytical path;
an analytical column provided on the analytical path, on a downstream side of the sample injection section, the analytical column being for separating the sample into each component; and
a detector provided on the analytical path, on a downstream side of the analytical column, the detector being for detecting the component separated by the analytical column.

7. The liquid feed pump according to claim 2, wherein the engineering plastic is a material selected from a group consisting of polyether ether ketone, and polytetrafluoroethylene.

8. The liquid feed pump according to claim 7, wherein the film of the acid-resistant material is formed also on a wall surface inside the pump chamber.

9. A liquid chromatograph comprising:
an analytical path;
the liquid feed pump according to claim 8, the liquid feed pump being for feeding a mobile phase to the analytical path;
a sample injection section for injecting a sample into the analytical path;
an analytical column provided on the analytical path, on a downstream side of the sample injection section, the analytical column being for separating the sample into each component; and
a detector provided on the analytical path, on a downstream side of the analytical column, the detector being for detecting the component separated by the analytical column.

10. A liquid chromatograph comprising:
an analytical path;
the liquid feed pump according to claim 7, the liquid feed pump being for feeding a mobile phase to the analytical path;
a sample injection section for injecting a sample into the analytical path;
an analytical column provided on the analytical path, on a downstream side of the sample injection section, the analytical column being for separating the sample into each component; and
a detector provided on the analytical path, on a downstream side of the analytical column, the detector being for detecting the component separated by the analytical column.

11. The liquid feed pump according to claim 2, wherein the film of the acid-resistant material is formed also on a wall surface inside the pump chamber.

12. A liquid chromatograph comprising:
an analytical path;
the liquid feed pump according to claim 11, the liquid feed pump being for feeding a mobile phase to the analytical path;
a sample injection section for injecting a sample into the analytical path;
an analytical column provided on the analytical path, on a downstream side of the sample injection section, the analytical column being for separating the sample into each component; and
a detector provided on the analytical path, on a downstream side of the analytical column, the detector being for detecting the component separated by the analytical column.

13. A liquid chromatograph comprising:
an analytical path;

the liquid feed pump according to claim 2, the liquid feed pump being for feeding a mobile phase to the analytical path;
a sample injection section for injecting a sample into the analytical path;
an analytical column provided on the analytical path, on a downstream side of the sample injection section, the analytical column being for separating the sample into each component; and
a detector provided on the analytical path, on a downstream side of the analytical column, the detector being for detecting the component separated by the analytical column.

14. The liquid feed pump according to claim 1, wherein the film of the acid-resistant material is formed also on a wall surface inside the pump chamber.

15. A liquid chromatograph comprising:
an analytical path;
the liquid feed pump according to claim 14, the liquid feed pump being for feeding a mobile phase to the analytical path;
a sample injection section for injecting a sample into the analytical path;
an analytical column provided on the analytical path, on a downstream side of the sample injection section, the analytical column being for separating the sample into each component; and
a detector provided on the analytical path, on a downstream side of the analytical column, the detector being for detecting the component separated by the analytical column.

16. A liquid chromatograph comprising:
an analytical path;
the liquid feed pump according to claim 1, the liquid feed pump being for feeding a mobile phase to the analytical path;
a sample injection section for injecting a sample into the analytical path;
an analytical column provided on the analytical path, on a downstream side of the sample injection section, the analytical column being for separating the sample into each component; and
a detector provided on the analytical path, on a downstream side of the analytical column, the detector being for detecting the component separated by the analytical column.

\* \* \* \* \*